US011766528B2

(12) United States Patent
Cheng et al.

(10) Patent No.: US 11,766,528 B2
(45) Date of Patent: Sep. 26, 2023

(54) SELECTIVE SEALING CARTRIDGE

(71) Applicant: L'Oreal, Paris (FR)

(72) Inventors: Wenzhen Cheng, Annadale, NJ (US); William Blake Soeters, Middletown, NJ (US)

(73) Assignee: L'Oreal, Paris (FR)

( * ) Notice: Subject to any disclaimer, the term of this patent is extended or adjusted under 35 U.S.C. 154(b) by 913 days.

(21) Appl. No.: 16/698,506

(22) Filed: Nov. 27, 2019

(65) Prior Publication Data

US 2021/0154417 A1    May 27, 2021

(51) Int. Cl.
  *A61M 11/06* (2006.01)
  *A61M 11/02* (2006.01)
  *A61M 39/24* (2006.01)
  *A61M 15/00* (2006.01)
  *A61M 16/14* (2006.01)
  *A61M 16/00* (2006.01)
  *A61M 16/20* (2006.01)

(52) U.S. Cl.
  CPC .............. *A61M 11/06* (2013.01); *A61M 11/02* (2013.01); *A61M 15/002* (2014.02); *A61M 16/0003* (2014.02); *A61M 16/14* (2013.01); *A61M 16/20* (2013.01); *A61M 39/24* (2013.01); *A61M 2202/04* (2013.01); *A61M 2205/123* (2013.01)

(58) Field of Classification Search
  CPC .... A61M 11/06; A61M 11/02; A61M 15/002; A61M 11/007; B05B 17/0638; A24F 40/40; A24F 40/42
  See application file for complete search history.

(56) References Cited

U.S. PATENT DOCUMENTS

| 9,162,004 | B1 | 10/2015 | Ansley et al. |
| 2007/0186923 | A1* | 8/2007 | Poutiatine ............... G16H 20/13 128/200.14 |
| 2011/0168175 | A1* | 7/2011 | Dunne ................... B65D 83/42 222/321.6 |
| 2012/0078197 | A1 | 3/2012 | O'Connor et al. |
| 2014/0110500 | A1* | 4/2014 | Crichton ............. B05B 17/0646 239/102.2 |
| 2018/0169288 | A1 | 6/2018 | Kelsen |

FOREIGN PATENT DOCUMENTS

JP          5014872 B2    8/2012

* cited by examiner

Primary Examiner — Margaret M Luarca
(74) Attorney, Agent, or Firm — Christensen O'Connor Johnson Kindness PLLC

(57) ABSTRACT

Cartridges have a cartridge body configured to store a formulation, a formulation valve disposed in the cartridge body, and an air valve disposed in the cartridge body. The cartridge is configured to dispense the formulation through the formulation valve when the formulation valve and the air valve are each in an open state, and to not dispense the formulation when the formulation valve and the air valve are in a closed state.

16 Claims, 5 Drawing Sheets

SELECTIVE SEALING CARTRIDGE

SUMMARY

In an aspect, the present disclosure provides a selective sealing cartridge having a cartridge body configured to store a formulation, a formulation valve disposed in the cartridge body, and an air valve disposed in the cartridge body. The cartridge is configured to dispense the formulation through the formulation valve when the formulation valve and the air valve are each in an open state, and to not dispense the formulation when the formulation valve and the air valve are in a closed state.

In some embodiments, the formulation valve and the air valve are biased toward the closed state, for example by a spring, an actuator, or the like. In some embodiments, a spring pushes an air valve seat toward an air valve body. In some embodiments, the cartridge includes a sliding internal member configured to move the air valve into the open state by pushing the spring. In some embodiments, the sliding internal member is a reservoir disposed in the cartridge body, the reservoir being configured to store the formulation. In some embodiments, the formulation valve is disposed in the reservoir. In some embodiments, the cartridge includes a cartridge cap that couples with the cartridge body, and the cartridge cap contacts the spring. The cartridge cap may include an alignment stud positioned to center the spring. In some embodiments, a single movement of the sliding internal member is configured to move the formulation valve into the open state and the air valve is moved into the open state. The cartridge may include an identifier corresponding to the formulation stored within the cartridge. The identifier may include at least one mechanical identifier formed in the cartridge body and/or at least one electronic component configured to output an electronic identifier of the formulation stored within the cartridge. In some embodiments, the cartridge includes the formulation stored in the cartridge body. In some embodiments, the cartridge body includes a coupling structure disposed on an outer surface thereof, the coupling structure being configured to couple with a complementary coupling structure of a device. In some embodiments, the cartridge body includes an alignment structure configured to guide correct coupling of the cartridge with a device. In some embodiments, the formulation valve and the air valve are disposed at a first end and a second end of the cartridge body, respectively.

In another aspect, the present disclosure provides a system having a nebulizer and a cartridge configured for reversible coupling with the nebulizer. The cartridge includes a cartridge body configured to store a formulation, a formulation valve disposed in the cartridge body, and an air valve disposed in the cartridge body. The cartridge is configured to dispense the formulation to the nebulizer through the formulation valve when the formulation valve and the air valve are in an open state, and to not dispense the formulation when the formulation valve and the air valve are in a closed state. In some embodiments, the nebulizer includes a nebulizing assembly configured to move the formulation valve and the air valve into the open state. In some embodiments, the nebulizing assembly includes a pushrod having an actuating member disposed thereon, the actuating member being configured to move the formulation valve and the air valve into the open state when the pushrod translates.

BRIEF DESCRIPTION OF THE SEVERAL VIEWS OF THE DRAWINGS

The foregoing aspects and many of the attendant advantages of the claimed subject matter will become more readily appreciated by reference to the following detailed description, when taken in conjunction with the accompanying drawings, wherein:

DETAILED DESCRIPTION

The present disclosure provides cartridges configured to be selectively and reversibly opened and closed. In one representative application, the inventive cartridges are part of a system configured to deliver a formulation (e.g., a cosmetic, pharmaceutical, or dermatological formulation) in aerosol form onto skin. For example, in one embodiment, the cartridge is a consumable sub-assembly configured for use with a device such as nebulizer. Representative nebulizers include those described in U.S. patent application Ser. No. 15/942,304, which is hereby incorporated by reference in its entirety. However, the inventive cartridges are useful both alone and in connection with additional devices beyond nebulizers.

The inventive cartridges are configured to be reversibly and selectively opened and closed (i.e., sealed), and formulation remaining in the cartridge does not leak from the cartridge when the cartridge is uncoupled from a device (e.g., a nebulizer). Additionally, exposure of formulation within the cartridge to the ambient environment is minimized or prevented entirely when the cartridge is closed, thereby preserving the formulation.

In the following description, numerous specific details are set forth in order to provide a thorough understanding of one or more embodiments of the present disclosure. It will be apparent to one skilled in the art, however, that many embodiments of the present disclosure may be practiced without some or all of the specific details. In some instances, well-known process steps have not been described in detail in order not to unnecessarily obscure various aspects of the present disclosure. Further, it will be appreciated that embodiments of the present disclosure may employ any combination of features described herein.

Figure 1:
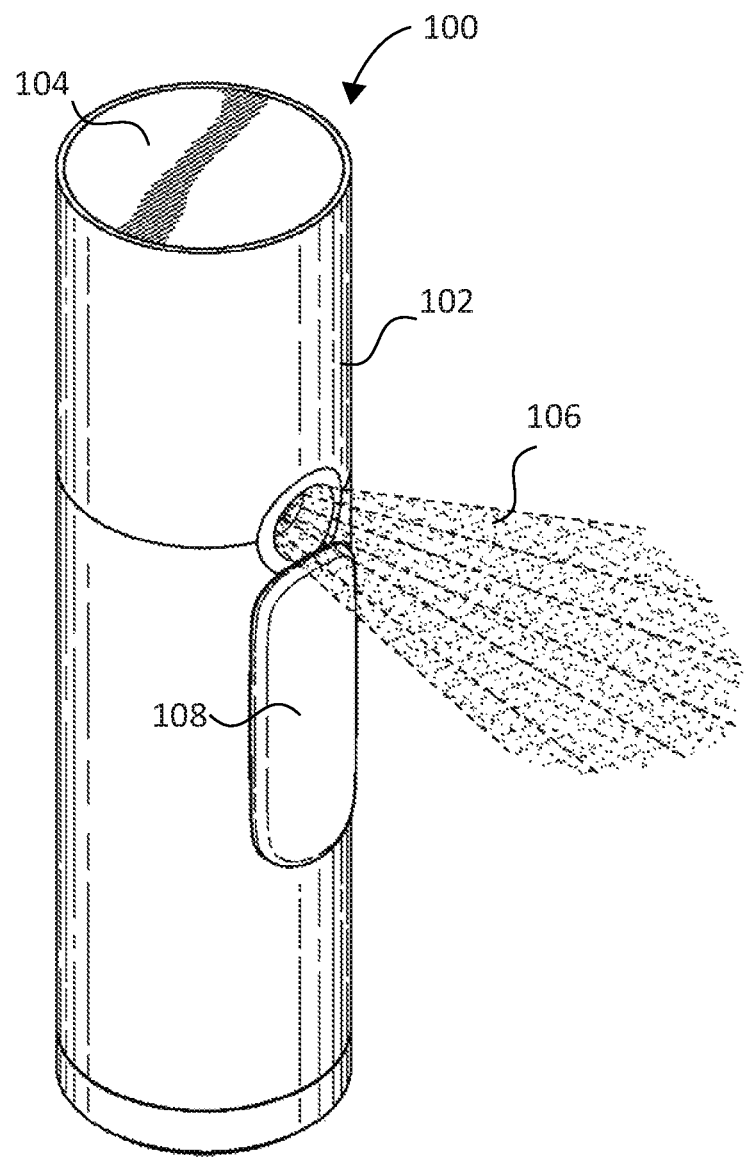
FIG. 1 shows an upper left perspective view of a system in accordance with one representative embodiment.
Figure 2:
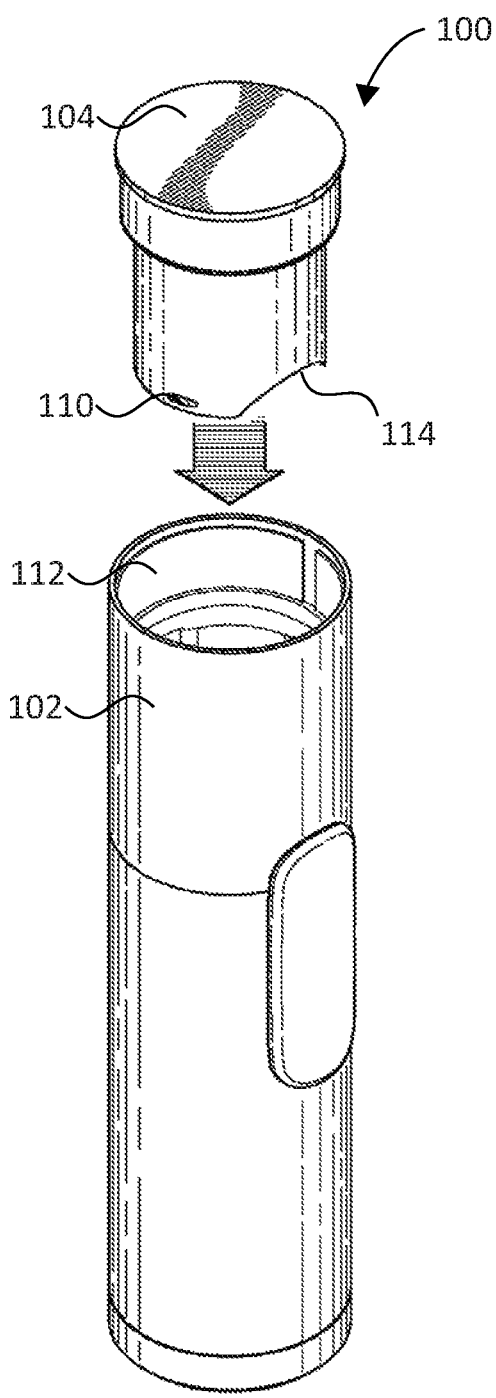
FIG. 2 shows a partially exploded upper left perspective view of the system of FIG. 1.

FIG. 1 and FIG. 2 illustrate a system 100 in accordance with a representative embodiment of the disclosure. System 100 includes a nebulizer 102 and a cartridge 104 that is configured for reversible coupling with the nebulizer 102. As shown in FIG. 1 and FIG. 2, the cartridge 104 is reversibly received by the nebulizer 102. As used herein, the cartridge 104 is reversibly coupled with the nebulizer 102 when it is securely coupled to the nebulizer 102, but may be removed without damaging either the nebulizer 102 or the cartridge 104. Further, the nebulizer 102 is configured to fluidically couple with a formulation contained within the cartridge 104 such that the nebulizer 102 can selectively discharge an aerosol 106 comprising the formulation. For example, in one representative method of use, a user activates a switch 108, which activates one or more valves and circuitry of a nebulizing assembly contained within the nebulizer 102, thereby causing the nebulizer 102 to discharge aerosol 106. Features of the nebulizer 102 and cartridge 104 that enable the fluidic coupling are described below in detail.

Figure 3:
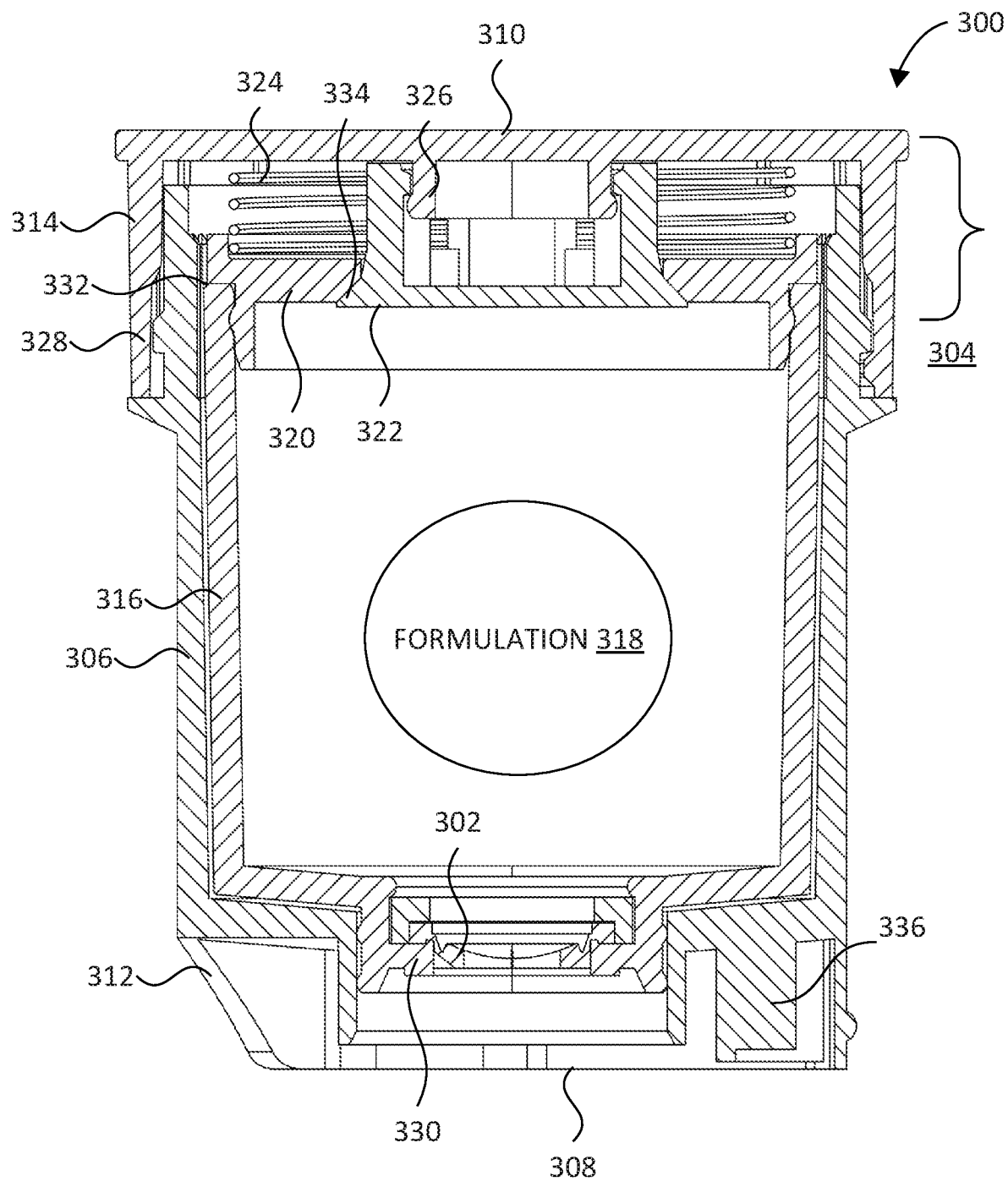
FIG. 3 shows a right side elevation section view of a cartridge in accordance with one representative embodiment.
Figure 4:
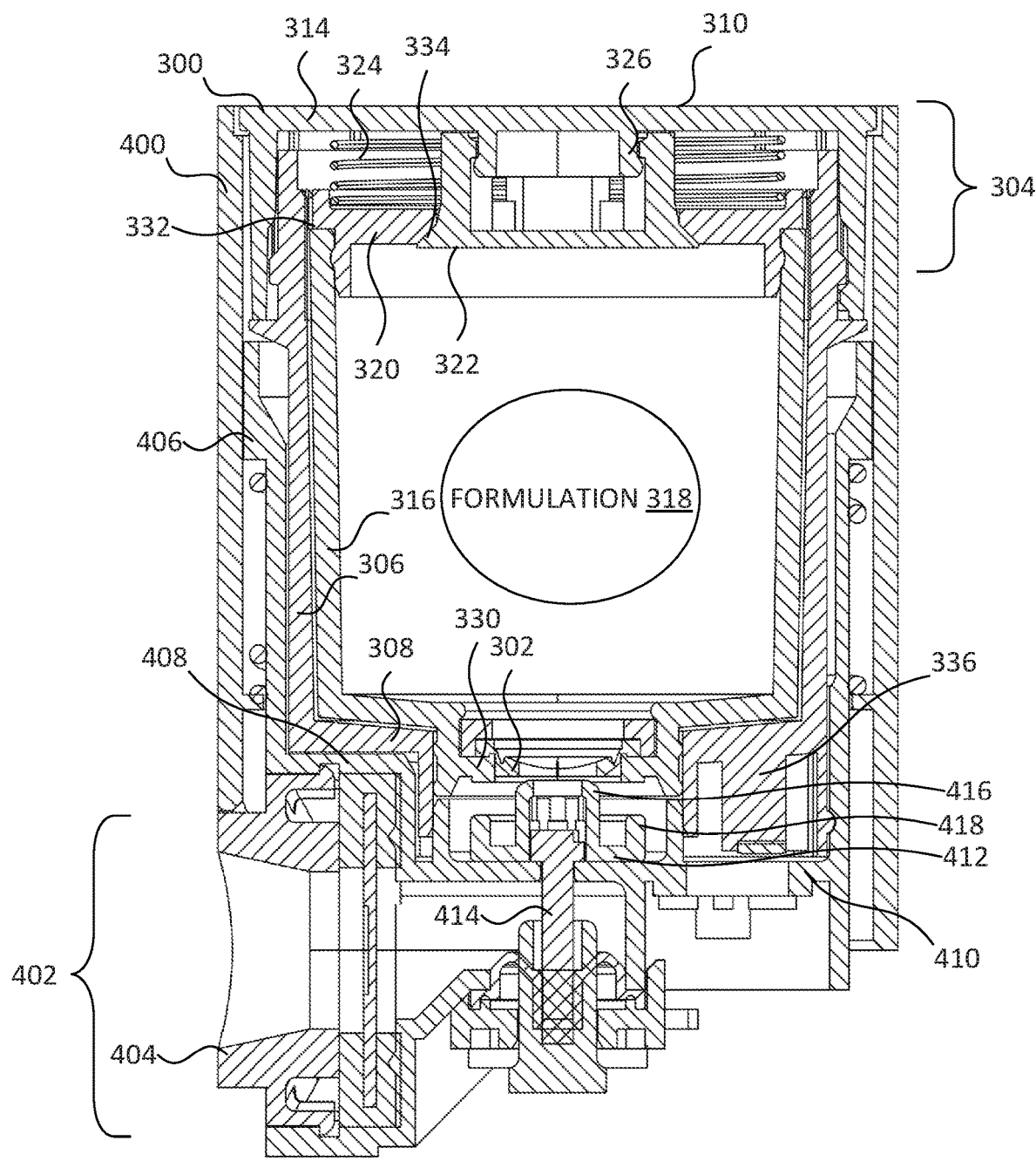
FIG. 4 illustrates a right side elevation section of the cartridge of FIG. 3, coupled with one representative device, with a formulation valve and an air valve of the cartridge in a closed state.

As shown in FIG. 2, cartridge 104 is configured for insertion into an opening 112 of nebulizer 102. The location of opening 112 is representative. In some embodiments, the opening 112 is located on another portion of the nebulizer 102. Cartridge 104 is reversibly coupled within nebulizer 102 such that it can be securely coupled to and selectively released from the nebulizer 102 one or more times. To facilitate this selective coupling, the representative cartridge 104 includes at least one coupling structure 110 disposed on an outer surface thereof. Accordingly, the nebulizer 102 includes at least one complementary coupling structure. In FIG. 1, the coupling structure 110 is a detent. In some embodiments, the nebulizer 102 and the cartridge 104 include other cooperatively-coupling structures, such as threads, latches, magnets, and the like.

FIG. 3 shows a representative cartridge 300 that is configured for selective and reversible coupling with a device such as nebulizer 102, and for selective and reversible opening, e.g., by the nebulizer 102. The cartridge 300 includes a number of useful features, including a formulation valve 302 and an air valve 304, the advantages of which will become apparent when described in detail below.

Cartridge 300 includes a cartridge body 306 that houses and protects additional components described below. Cartridge body 306 has a hollow, open-ended shape with a first end 308 and a second end 310, the first end 308 being configured for insertion into a device before the second end 310. As used herein, the first end 308 and second end 310 may be used to orient description of other aspects of the cartridge 300, not just the cartridge body 306. The second end 310 is open-ended and configured to be enclosed by a cartridge cap 314 that couples with cartridge body 306. In some embodiments, cartridge body 306 is formed from a thermoplastic polymer such as polypropylene, polyethylene, or the like. In FIG. 3, cartridge body 306 is generally cylindrical to facilitate insertion into a cylindrical device (e.g., the nebulizer 102 of FIG. 1). Accordingly, cartridge body 306 has an annular outer wall (where 302 points in FIG. 3). In some embodiments, cartridge body 306 is another shape, e.g., rectangular, conical, oval-shaped, and the like. In some embodiments, one or more components of the cartridge 300 are recyclable, biodegradable, or compostable, e.g., to facilitate re-use and/or recycling. Separately, cartridge 300 includes an alignment structure 312 proximal first end 308 that is configured to guide correct coupling of the cartridge 300 with a device. In FIG. 3, alignment structure 312 is an arcuate cut-out from cartridge body 306, the cut-out has a shape and size that are complementary to a device (e.g., nebulizer 102 of FIG. 1). In some embodiments, alignment structure 312 is located proximal second end 310 or at an intermediate position along cartridge body 306. In some embodiments, alignment structure 312 has a different shape or size than shown in FIG. 3, e.g., a raised portion.

Cartridge cap 314 is formed from a similar material as cartridge body 306, and encloses a number of elements within the cartridge body 306, including the formulation valve 302, a reservoir 316, a formulation 318, a reservoir cap 320, an air valve body 322, and a spring 324. Certain of the foregoing elements comprise the air valve 304, as described below. Cartridge cap 314 has an annular outer wall that fits over the open end of the cartridge body 306. In some embodiments, the cartridge cap 314 is configured to fit within the open end of the cartridge body 306, rather than over it. To align elements of the air valve 304, the cartridge cap 314 includes an alignment stud 326 that extends away from a center of the cartridge cap 314. In some embodiments, the alignment stud 326 is positioned off-center on the cartridge cap 314. Cartridge cap 314 and cartridge body 306 include complementary engagement members 328 in order to retain cartridge cap 314 on the cartridge body 306. In some embodiments, cartridge body 306 and cartridge cap 314 are configured to be a permanent assembly. In some embodiments, engagement members 328 are configured such that cartridge cap 314 can be selectively decoupled from cartridge body 306.

Reservoir 316 is disposed within the cartridge body 306 and is configured to store the formulation 318 (e.g., a liquid cosmetic, pharmaceutical, or dermatological formulation). In addition, reservoir 316 operates as a sliding internal member configured to translate within cartridge body 306 between the first end 308 and the second end 310. For example, in some embodiments, a device (e.g., the nebulizer 102 of FIG. 1) is configured to push against a shoulder 330 of the reservoir 316, causing the reservoir 316 to translate toward the second end 310 of cartridge 300 and to push against a shoulder 332 of the reservoir cap 320. In some embodiments, the reservoir 316 is configured to store about 5 ml to about 50 ml of a liquid formulation, e.g., about 8 ml, about 10 ml, or any other volume in that range. In FIG. 3, the reservoir 316 has a hollow, open-ended shape. The open end of reservoir 316 is configured to be at least partially enclosed by a reservoir cap 320, which forms part of the air valve 304 as described below. In particular, reservoir cap 320 has an annular shape with an opening therethrough, and the inner surface of that opening forms an air valve seat 334 that seats against the air valve body 322 when the air valve is in a closed state. A first side of the reservoir cap 320 is configured to act as a base for a spring 324 that forms part of the air valve 304, as described below. A second side of the reservoir cap 320 (in particular the shoulder 332) is configured to engage the reservoir 316.

In FIG. 3, the cartridge 300 includes an optional identifier 336 formed integrally with the cartridge 300, the identifier 336 being configured to convey information to a device (e.g., the nebulizer 102) about the formulation 318 stored within the cartridge 300. In FIG. 3, identifier 336 is disposed proximal to the first end 308, and is a mechanical identifier having one or more mechanical features (e.g., one or more fingers or raised portions) that identify the formulation 318 contained within cartridge 300. For example, in some embodiments, a device includes one or more switches configured to receive the identifier 336 and to determine the formulation 318 based upon the one or more mechanical features. In some embodiments, the identifier 336 includes at least one electronic component configured to output an electronic identifier of the formulation 318 stored within the cartridge 300.

As mentioned above, cartridge 300 includes the formulation valve 302 and the air valve 304. Formulation valve 302 is disposed proximal to the first end 308 and is selectively movable between an open state and a closed state. To prevent leaks, formulation valve 302 is biased toward a closed state as described below. When in the closed state, the formulation valve 302 is configured to prevent passage of the formulation 318 therethrough. When in the open state, formulation valve 302 is configured to allow passage of the formulation 318 therethrough, in particular when the air valve 304 is also in an open state, as described below. In FIG. 3, the formulation valve 302 is shown in the closed state and is a diaphragm-type valve, such as may be formed from silicone, rubber, or the like. In the representative embodiment of FIG. 3, the formulation valve 302 is configured to be moved from the closed state to the open state by a device, such as an actuating member of a nebulizer as described below. In FIG. 3, formulation valve 302 is disposed in the reservoir 316. In some embodiments, formulation valve 302 is disposed directly in the cartridge body 306.

Air valve 304 is an assembly that selectively allows air (or other gas) to pass to/from reservoir 316 when it is in an open state, for example when formulation valve 302 is also in an open state. Advantageously, this enables smoother dispensation of formulation 318 from reservoir 316. Air valve 304 includes the reservoir cap 320, air valve body 322, and spring 324. In FIG. 3, reservoir cap 320 covers the open end of reservoir 316, and provides the shoulder 332 that reservoir 316 can push against (e.g., due to the pushing action of another device such as the nebulizer 102 of FIG. 1). As mentioned above, reservoir cap 320 has an annular shape with an opening therethrough. The perimeter of this opening forms the air valve seat 334, which the air valve body 322 seats against when air valve 304 is in the closed state to form a fluid-tight seal. Air valve body 322 is mounted on the alignment stud 326 of cartridge cap 314 and extends through the opening of reservoir cap 320, with a flared end disposed toward first end 308. To prevent leaks, air valve 304 is biased toward the closed state by spring 324, which pushes reservoir cap 320 toward first end 308 such that air valve seat 334 forms a fluid-tight seal against air valve body 322 unless a translational force exerted by reservoir 316 on the shoulder 332 of reservoir cap 320 overcomes the opposite spring force of spring 324. Thus, reservoir cap 320 is a base for spring 324.

Thus, cartridge 300 includes formulation valve 302 and air valve 304, both of which are selectively and reversibly movable between a closed state and an open state. When formulation valve 302 or air valve 304 are in the closed state, fluid (including formulation 318) cannot escape the cartridge 300 and is securely stored therein. When formulation valve 302 and air valve 304 are in the open state, fluid can pass through that valve via formulation valve 302. Both formulation valve 302 and air valve 304 are biased to the closed state such that no fluid can escape from reservoir 316 (i.e., be dispensed from) unless one or both valves are moved into the open state. While it is possible for either formulation valve 302 or air valve 304 to be moved from the closed state to the open state independently, both valves are configured to open or close more or less at the same time in response to a force exerted by a device (e.g., by the nebulizer 102 of FIG. 1), as described below. That is, formulation valve 302 is mechanically connected to air valve 304 by the outer wall of reservoir 316 such that when a device moves formulation valve 302 from the closed state to the open state, the device also causes the reservoir 316 to translate and push against reservoir cap 320, thereby moving the air valve 304 from the closed state to the open state. In some embodiments, one or both of the formulation valve 302 or the air valve 304 are configured such that the formulation valve 302 is moved into the open state before the air valve 304. In some embodiments, one or both of the formulation valve 302 or the air valve 304 are configured such that the formulation valve 302 is moved into the open state after the air valve 304.

FIG. 4 and FIG. 5 show the cartridge 300 of FIG. 3 coupled with a portion of a nebulizer 400 that is similar to the nebulizer 102 of FIG. 1. In FIG. 4, both the formulation valve 302 and air valve 304 are in the closed state. In FIG. 5, both the formulation valve 302 and air valve 304 are in the open state. Nebulizer 400 includes a nebulizing assembly 402 that forms a reversible fluidic connection with cartridge 300 such that, under certain circumstances, the nebulizing assembly 402 moves the formulation valve 302 and air valve 304 from the closed state into the open state, receives formulation 318 from the cartridge 300, and discharges the formulation 318 as an aerosol from a nozzle 404. In some embodiments, nebulizer 400 includes at least some features of the nebulizer 102 of FIG. 1.

Cartridge 300 is reversibly and selectively coupled within a cartridge cradle 406 formed in the body of nebulizer 400. The cartridge cradle 406 includes a hollow cavity that is sized and shaped to receive and securely hold the cartridge 300 therein. The cartridge cradle 406 includes coupling structure that is complementary to coupling structure of cartridge 300 (such as the coupling structure 110 shown in FIG. 2). In addition, cartridge cradle 406 includes an alignment structure 408 and an identifier receiver 410. The alignment structure 408 has a complementary shape to the alignment structure 312 of cartridge 300 (see FIG. 3 and FIG. 2). The identifier receiver 410 is configured to receive identifier 336 of the cartridge 300. In some embodiments, identifier receiver 410 includes one or more switches or other electronic components that are triggered by the identifier 336 upon insertion of the cartridge 300 into the cartridge cradle 406.

Nebulizing assembly 402 includes an actuating member 412 connected to a pushrod 414. Actuating member 412 is configured both to open the formulation valve 302 and to push against the shoulder 330 of the cartridge 300, in order to move the formulation valve 302 and the air valve 304 from the closed state into the open state as described below. That is, actuating member 412 includes a formulation valve actuating portion 416 and an air valve actuating portion 418. In FIG. 4 and FIG. 5, the formulation valve actuating portion 416 is a male portion having a complementary shape to the formulation valve 302 such that it can be inserted into the formulation valve 302. The formulation valve actuating portion 416 has an annular shape with a central orifice configured to fluidically connect the formulation 318 to the nebulizing assembly 402 when the formulation valve 302 is in the open state. In FIG. 4 and FIG. 5, the air valve actuating portion 418 is an annular shoulder that is sized and positioned to push against the shoulder 330 of the cartridge 300. In some embodiments, actuating member 412 has a different shape and size, but is nevertheless configured to move the formulation valve 302 and air valve 304 from the closed state into the open state.

The pushrod 414 is connected to an actuator (not shown), which in turn is controlled by circuitry and logic of the nebulizing assembly 402. In use, a user undertakes an action (such as activating a switch similar to switch 108 shown in FIG. 1), which in turn causes the circuitry, logic, and actuator to translate the pushrod 414 between a "downward" and "upward" position (using the page of FIG. 4 as a directional reference, and corresponding generally to first end 308 and second end 310).

In FIG. 4, the pushrod 414 is in the "downward" or "retracted" position that corresponds with the closed state of the cartridge 300. As discussed above, the formulation valve 302 and air valve 304 of the cartridge 300 are biased to the closed state, and this is shown in FIG. 4. As shown, the formulation valve actuating portion 416 does not contact the formulation valve 302, and therefore the formulation valve 302 remains in the closed state. Also, the air valve actuating portion 418 does not contact the shoulder 330 of the cartridge 300, and therefore the air valve 304 remains in the closed state as result of the spring force exerted by spring 324 on the reservoir cap 320, which causes the air valve seat 334 to seat against the air valve body 322. Thus, the formulation 318 cannot escape (i.e., be dispensed from) the cartridge 300.

Figure 5:
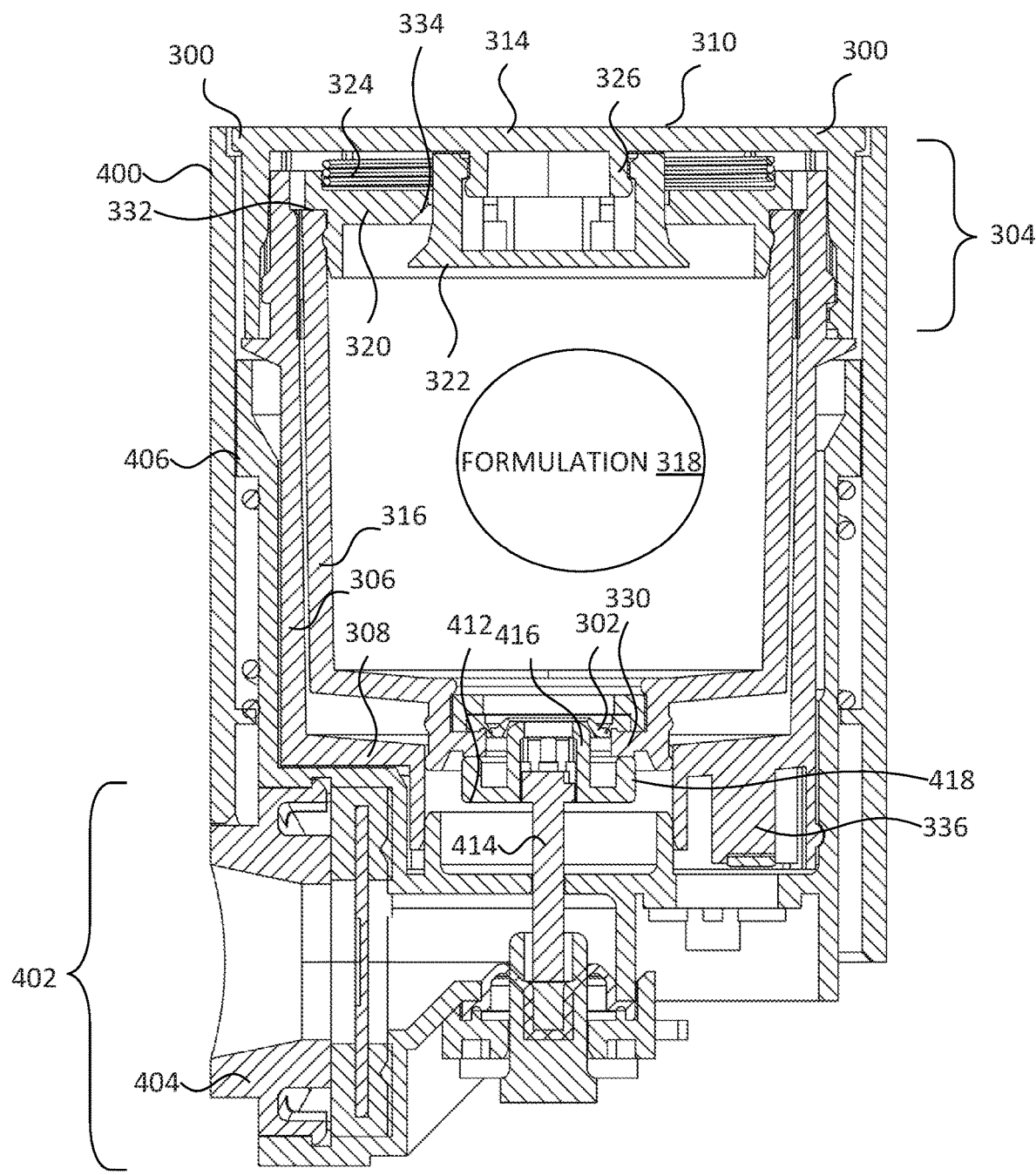
FIG. 5 illustrates a right side elevation section of the cartridge of FIG. 3, coupled with the device of FIG. 4, with the formulation valve and the air valve of the cartridge in an open state.

In FIG. 5, the pushrod 414 is in the "upward" or "extended" position that corresponds with the open state of the cartridge 300. The translational distance between the "retracted" and "extended" state may be about 1 cm to about 10 cm. As shown, the formulation valve actuating portion 416 of the actuating member 412 extends through the formulation valve 302, thus moving the formulation valve 302 from the closed state to the open state. As mentioned above, the formulation valve actuating portion 416 has a central orifice that establishes a fluidic connection between the formulation 318 and the nebulizing assembly 402 when the formulation valve 302 is in the open state. Generally, the cartridge 300 and nebulizing assembly 402 are configured such that the fluidic connection is fluid-tight in order to prevent leakage of the formulation 318. In addition, the air valve actuating portion 418 pushes against the shoulder 330 of the cartridge 300 such that it causes the reservoir 316 to translate within the cartridge 300, which pushes against the shoulder 332 of the reservoir cap 320 and overcomes the spring force of spring 324, thereby causing the air valve seat 334 to unseat from air valve body 322. When the air valve seat 334 becomes unseated from the air valve body 322, the air valve 304 moves from the closed state to the open state, and an interior cavity of the reservoir 316 becomes fluidically connected with the ambient environment, e.g., through an air vent in cartridge 300. In some embodiments, the air valve seat 334 moves away from the air valve body 322 about 1 mm to about 10 mm. Due to the fluidic connection between the formulation 318 and the nebulizing assembly 402, and between the reservoir 316 and the ambient environment, the formulation 318 can escape (i.e., be dispensed from) the cartridge 300 when both the formulation valve 302 and the air valve 304 are in the open state. For example, when the second end 310 of the cartridge 300 is held gravitationally above the first end 308, formulation 318 can escape via the formulation valve 302 and the formulation valve actuating portion 416 into the nebulizing assembly 402, ultimately being dispensed as an aerosol through the nozzle 404. In some embodiments, the formulation valve 302, the actuating member 412, and/or the actuating member 412 are configured such that the formulation valve 302 and the air valve 304 move into the open state at about the same time. In some embodiments, the formulation valve 302, the actuating member 412, and/or the actuating member 412 are configured such that the formulation valve 302 moves into the open state before the air valve 304.

When the pushrod 414 moves back into the "retracted" position (e.g., under control of circuitry of the nebulizing assembly 402), the formulation valve 302 and the air valve 304 revert to the closed state, and once again the formulation 318 can no longer escape (i.e., be dispensed from) the cartridge 300.

Thus, the cartridges of the present disclosure advantageously provide for selective and reversible coupling with devices such as nebulizers, and furthermore provide selective opening and closing, thereby enable secure storage of formulations stored therein. In addition, the inventive cartridges allow smooth and precise dispensation of formulations therefrom, e.g., under control of another device.

Embodiments disclosed herein may utilize circuitry in order to implement technologies and methodologies described herein, operatively connect two or more components, generate information, determine operation conditions, control an appliance, device, or method, and/or the like. Circuitry of any type can be used. In an embodiment, circuitry includes, among other things, one or more computing devices such as a processor (e.g., a microprocessor), a central processing unit (CPU), a digital signal processor (DSP), an application-specific integrated circuit (ASIC), a field-programmable gate array (FPGA), or the like, or any combinations thereof, and can include discrete digital or analog circuit elements or electronics, or combinations thereof.

In an embodiment, circuitry includes one or more ASICs having a plurality of predefined logic components. In an embodiment, circuitry includes one or more FPGA having a plurality of programmable logic components. In an embodiment, circuitry includes hardware circuit implementations (e.g., implementations in analog circuitry, implementations in digital circuitry, and the like, and combinations thereof). In an embodiment, circuitry includes combinations of circuits and computer program products having software or firmware instructions stored on one or more computer readable memories that work together to cause a device to perform one or more methodologies or technologies described herein. In an embodiment, circuitry includes circuits, such as, for example, microprocessors or portions of microprocessor, that require software, firmware, and the like for operation. In an embodiment, circuitry includes an implementation comprising one or more processors or portions thereof and accompanying software, firmware, hardware, and the like. In an embodiment, circuitry includes a baseband integrated circuit or applications processor integrated circuit or a similar integrated circuit in a server, a cellular network device, other network device, or other computing device. In an embodiment, circuitry includes one or more remotely located components. In an embodiment, remotely located components are operatively connected via wireless communication. In an embodiment, remotely located components are operatively connected via one or more receivers, transmitters, transceivers, or the like.

An embodiment includes one or more data stores that, for example, store instructions or data. Non-limiting examples of one or more data stores include volatile memory (e.g., Random Access memory (RAM), Dynamic Random Access memory (DRAM), or the like), non-volatile memory (e.g., Read-Only memory (ROM), Electrically Erasable Programmable Read-Only memory (EEPROM), Compact Disc Read-Only memory (CD-ROM), or the like), persistent memory, or the like. Further non-limiting examples of one or more data stores include Erasable Programmable Read-Only memory (EPROM), flash memory, or the like. The one or more data stores can be connected to, for example, one or more computing devices by one or more instructions, data, or power buses.

In an embodiment, circuitry includes one or more computer-readable media drives, interface sockets, Universal Serial Bus (USB) ports, memory card slots, or the like, and one or more input/output components such as, for example, a graphical user interface, a display, a keyboard, a keypad, a trackball, a joystick, a touch-screen, a mouse, a switch, a dial, or the like, and any other peripheral device. In an embodiment, circuitry includes one or more user input/output components that are operatively connected to at least one computing device to control (electrical, electromechanical, software-implemented, firmware-implemented, or other control, or combinations thereof) one or more aspects of the embodiment.

In an embodiment, circuitry includes a computer-readable media drive or memory slot configured to accept signal-bearing medium (e.g., computer-readable memory media, computer-readable recording media, or the like). In an embodiment, a program for causing a system to execute any of the disclosed methods can be stored on, for example, a computer-readable recording medium (CRMM), a signal-bearing medium, or the like. Non-limiting examples of signal-bearing media include a recordable type medium such as any form of flash memory, magnetic tape, floppy disk, a hard disk drive, a Compact Disc (CD), a Digital Video Disk (DVD), Blu-Ray Disc, a digital tape, a computer memory, or the like, as well as transmission type medium such as a digital and/or an analog communication medium (e.g., a fiber optic cable, a waveguide, a wired communications link, a wireless communication link (e.g., transmitter, receiver, transceiver, transmission logic, reception logic, etc.). Further non-limiting examples of signal-bearing media include, but are not limited to, DVD-ROM, DVD-RAM, DVD+RW, DVD-RW, DVD-R, DVD+R, CD-ROM, Super Audio CD, CD-R, CD+R, CD+RW, CD-RW, Video Compact Discs, Super Video Discs, flash memory, magnetic tape, magneto-optic disk, MINIDISC, non-volatile memory card, EEPROM, optical disk, optical storage, RAM, ROM, system memory, web server, or the like.

The detailed description set forth above in connection with the appended drawings, where like numerals reference like elements, are intended as a description of various embodiments of the present disclosure and are not intended to represent the only embodiments. Each embodiment described in this disclosure is provided merely as an example or illustration and should not be construed as preferred or advantageous over other embodiments. The illustrative examples provided herein are not intended to be exhaustive or to limit the disclosure to the precise forms disclosed. Similarly, any steps described herein may be interchangeable with other steps, or combinations of steps, in order to achieve the same or substantially similar result. Generally, the embodiments disclosed herein are non-limiting, and the inventors contemplate that other embodiments within the scope of this disclosure may include structures and functionalities from more than one specific embodiment shown in the figures and described in the specification.

In the foregoing description, specific details are set forth to provide a thorough understanding of exemplary embodiments of the present disclosure. It will be apparent to one skilled in the art, however, that the embodiments disclosed herein may be practiced without embodying all the specific details. In some instances, well-known process steps have not been described in detail in order not to unnecessarily obscure various aspects of the present disclosure. Further, it will be appreciated that embodiments of the present disclosure may employ any combination of features described herein.

The present application may include references to directions, such as "vertical," "horizontal," "front," "rear," "left," "right," "top," and "bottom," etc. These references, and other similar references in the present application, are intended to assist in helping describe and understand the particular embodiment (such as when the embodiment is positioned for use) and are not intended to limit the present disclosure to these directions or locations.

The present application may also reference quantities and numbers. Unless specifically stated, such quantities and numbers are not to be considered restrictive, but exemplary of the possible quantities or numbers associated with the present application. Also in this regard, the present application may use the term "plurality" to reference a quantity or number. In this regard, the term "plurality" is meant to be any number that is more than one, for example, two, three, four, five, etc. The term "about," "approximately," etc., means plus or minus 5% of the stated value. The term "based upon" means "based at least partially upon."

The principles, representative embodiments, and modes of operation of the present disclosure have been described in the foregoing description. However, aspects of the present disclosure, which are intended to be protected, are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure as claimed.

What is claimed is:

1. A cartridge, comprising:
   a cartridge body configured to store a formulation;
   a formulation valve disposed in the cartridge body; and
   an air valve disposed in the cartridge body,
   wherein the cartridge is configured to dispense the formulation through the formulation valve when the formulation valve and the air valve are each in an open state, and to not dispense the formulation when the formulation valve and the air valve are in a closed state, wherein a liquid formulation moves freely within the cartridge body, and the formulation valve is disposed on a side of the cartridge where the liquid formulation accumulates within the cartridge body, wherein the formulation valve and the air valve are biased toward the closed state, wherein the air valve is biased toward the closed state by a spring, and wherein the spring pushes an air valve seat toward an air valve body.

2. The cartridge of claim 1, the cartridge further comprising a sliding internal member configured to move the air valve into the open state by pushing the spring.

3. The cartridge of claim 2, wherein the sliding internal member is a reservoir disposed in the cartridge body, the reservoir being configured to store the formulation.

4. The cartridge of claim 3, wherein the formulation valve is disposed in the reservoir.

5. The cartridge of claim 2, wherein a single movement of the sliding internal member is configured to move the formulation valve into the open state and the air valve is moved into the open state.

6. The cartridge of claim 1, wherein the cartridge comprises an identifier corresponding to the formulation stored within the cartridge.

7. The cartridge of claim 6, wherein the identifier comprises at least one mechanical identifier formed in the cartridge body.

8. The cartridge of claim 1, further comprising the formulation stored in the cartridge body.

9. The cartridge of claim 1, wherein the cartridge body includes a coupling structure disposed on an outer surface thereof, the coupling structure being configured to couple with a complementary coupling structure of a device.

10. The cartridge of claim 1, wherein the cartridge body includes an alignment structure configured to guide correct coupling of the cartridge with a device.

11. The cartridge of claim 1, wherein the formulation valve and the air valve are disposed at a first end and a second end of the cartridge body, respectively.

12. A cartridge, comprising:
a cartridge body configured to store a formulation;
a formulation valve disposed in the cartridge body; and
an air valve disposed in the cartridge body,
wherein the cartridge is configured to dispense the formulation through the formulation valve when the formulation valve and the air valve are each in an open state, and to not dispense the formulation when the formulation valve and the air valve are in a closed state, wherein a liquid formulation moves freely within the cartridge body, and the formulation valve is disposed on a side of the cartridge where the liquid formulation accumulates within the cartridge body, wherein the formulation valve and the air valve are biased toward the closed state, wherein the air valve is biased toward the closed state by a spring, further comprising a cartridge cap that couples with the cartridge body, the cartridge cap contacting the spring.

13. The cartridge of claim 12, wherein the cartridge cap includes an alignment stud positioned to center the spring.

14. A system, comprising:
a nebulizer; and
a cartridge configured for reversible coupling with the nebulizer, the cartridge comprising:
a cartridge body configured to store a formulation;
a formulation valve disposed in the cartridge body; and
an air valve disposed in the cartridge body,
wherein the cartridge is configured to dispense the formulation to the nebulizer through the formulation valve when the formulation valve and the air valve are in an open state, and to not dispense the formulation when the formulation valve and the air valve are in a closed state, wherein a liquid formulation moves freely within the cartridge body, and the formulation valve is disposed on a side of the cartridge where the liquid formulation accumulates within the cartridge body, wherein the formulation valve and the air valve are biased toward the closed state, wherein the air valve is biased toward the closed state by a spring, and wherein the spring pushes an air valve seat toward an air valve body.

15. The system of claim 14, wherein the nebulizer comprises a nebulizing assembly configured to move the formulation valve and the air valve into the open state.

16. The system of claim 15, wherein the nebulizing assembly comprises a pushrod having an actuating member disposed thereon, the actuating member being configured to move the formulation valve and the air valve into the open state when the pushrod translates.

* * * * *